United States Patent [19]

Gold et al.

[11] Patent Number: 4,481,953

[45] Date of Patent: Nov. 13, 1984

[54] ENDOCARDIAL LEAD HAVING HELICALLY WOUND RIBBON ELECTRODE

[75] Inventors: Philip Gold, Pompano Beach; Peter P. Tarjan, Miami, both of Fla.

[73] Assignee: Cordis Corporation, Miami, Fla.

[21] Appl. No.: 566,573

[22] Filed: Dec. 29, 1983

Related U.S. Application Data

[63] Continuation of Ser. No. 320,410, Nov. 12, 1981.

[51] Int. Cl.³ .............................................. A61N 1/00
[52] U.S. Cl. ........................... 128/786; 128/419 D; 128/419 P; 128/642
[58] Field of Search ............... 128/419 D, 419 P, 642, 128/783-786

[56] References Cited

U.S. PATENT DOCUMENTS

| | | | |
|---|---|---|---|
| 3,367,339 | 2/1968 | Sessions | 128/418 |
| 3,568,660 | 3/1971 | Crites | 128/2 |
| 3,572,344 | 3/1971 | Bolduc | 128/418 |
| 3,664,347 | 5/1972 | Harmjanz | 128/419 P X |
| 3,769,984 | 11/1973 | Muench | 128/404 |
| 3,788,329 | 1/1974 | Friedman | 128/404 |
| 3,825,015 | 7/1974 | Berkovits | 128/404 |
| 3,942,536 | 3/1976 | Mirowski et al. | 128/419 D |
| 3,995,623 | 12/1976 | Blake et al. | 128/2.06 E |
| 4,161,952 | 7/1979 | Kinney et al. | 128/786 |
| 4,271,847 | 6/1981 | Stokes | 128/786 |

OTHER PUBLICATIONS

Elecath Cardiovascular Catheters and Instruments, 1972, 26 pp.

*Primary Examiner*—William E. Kamm
*Assistant Examiner*—Christine A. Fukushima
*Attorney, Agent, or Firm*—Henry W. Collins; Thomas R. Vigil

[57] ABSTRACT

An endocardial lead which includes an elongated, flexible, insulative tubing, a central flexible conductor positioned within the tubing and having one end adapted to be electrically connected to a pulse generator. A ribbon-shaped bonding member is connected to the other end of the central conductor. The ribbon-shaped bonding member extends through an aperture in the wall of the insulative tubing and is positioned along the outer surface of the tubing. A ribbon-shaped electrode is helically wound around the outer surface of the insulative tubing and positioned over the ribbon-shaped bonding member. With this configuration, a low impedance electrical connection is provided between the ribbon-shaped electrode and the central conductor, and between adjacent turns of the electrode.

6 Claims, 4 Drawing Figures

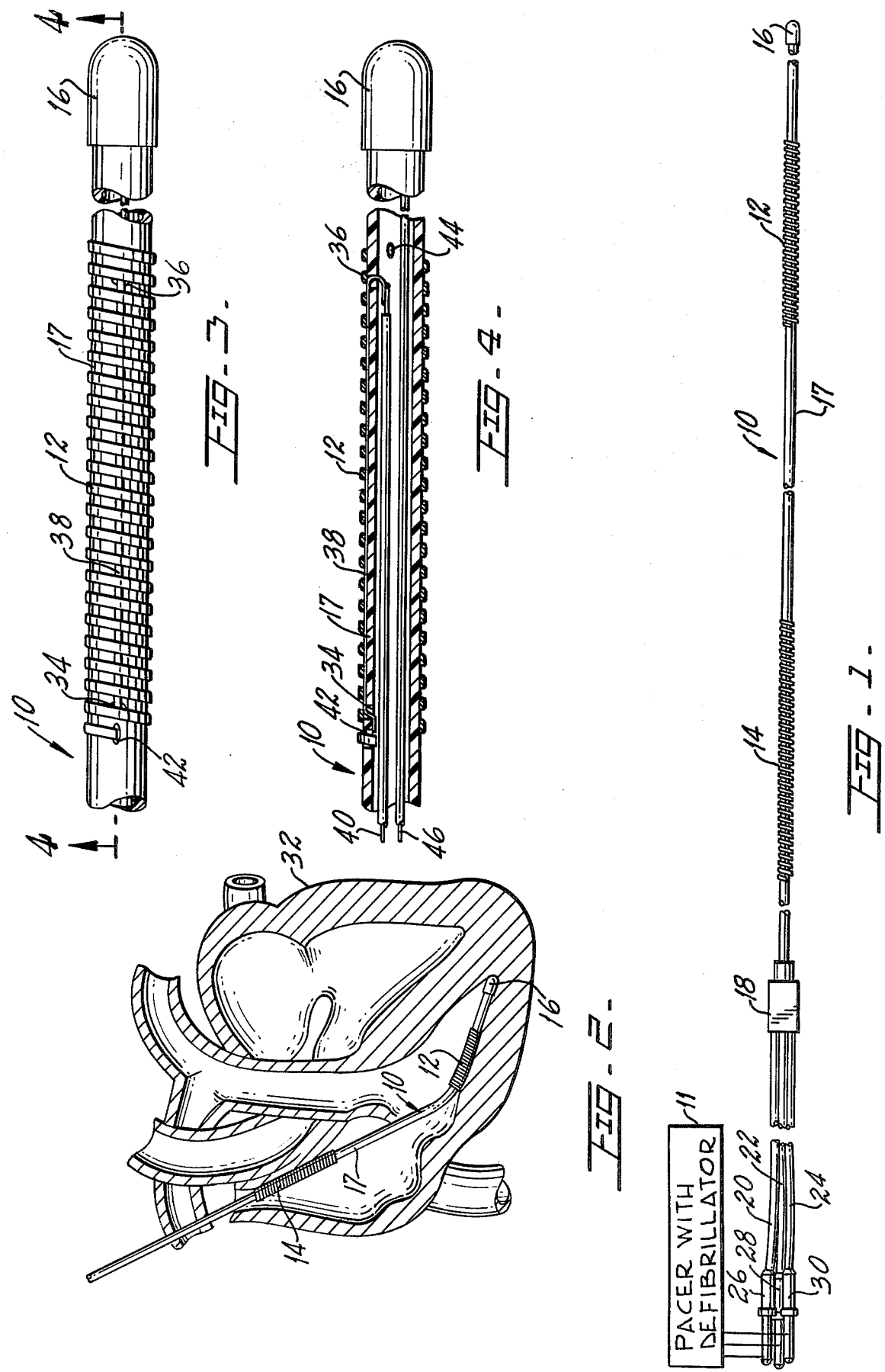

ENDOCARDIAL LEAD HAVING HELICALLY WOUND RIBBON ELECTRODE

This is a continuation of application Ser. No. 320,410, filed Nov. 12, 1981.

BACKGROUND OF THE INVENTION

It is known that when arrhythmias, such as ventricular fibrillation, occur this condition may be corrected by applying a high energy electrical current through the myocardium. Oftentimes this procedure is accomplished by means of chest paddles which are appropriately placed on the thorax of the patient, or by electrodes applied directly to the surface of the heart during open heart surgery. It is also known that ventricular defibrillation can be carried out by use of a temporary or a permanently implanted endocardial lead.

For example, one type of endocardial lead utilized for defibrillation includes two electrodes positioned on a single lead for applying a voltage to the myocardium for a fraction of a second. If the voltage is sufficient to depolarize the fibrillating portion of the myocardium, the heart is returned to a normal cardiac rhythm.

One of the advantages of an endocardial lead for performing a defibrillation procedure is that the energy requirements are substantially less than that required for external paddle defibrillators. One of the problems associated with present endocardial defibrillator leads is that with the high electrical energy which must be applied, there is a corresponding high current density established at the electrodes. With the high impedance associated with electrodes of relatively small surface area, it is difficult to deliver the required energy to the myocardium to provide effective defibrillation. If the electrodes are increased in size to thereby increase their surface area, the electrodes tend to form rigid segments in the defibrillator lead thereby reducing the flexibility of the lead.

In order for the defibrillator lead to be either temporarily or permanently implanted in a patient, the lead must be capable of withstanding repeated bending and torsional stresses. In addition, the electrodes must have relatively large surface areas in order to deliver the high levels of energy that are required for defibrillation. In addition, the defibrillator lead must also be biocompatible, as well as of a configuration such that the lead has a smooth outer surface in order to prevent damage to adjacent tissue when the lead is inserted or withdrawn from the venous system of the patient.

SUMMARY OF THE INVENTION

The present invention is generally related to the field of cardiac pacing and treatment of arrhythmic heart conditions, and more specifically to an endocardial lead for performing these functions.

The endocardial lead of the present invention includes an elongated, flexible, insulative tubing having proximal and distal ends. The tubing includes at least one aperture extending through the wall of tubing at a predetermined position along the length of the tubing. An elongated, flexible conductor is positioned within the insulative tubing. The conductor has an insulative coating which surrounds the conductor over substantially the entire length of the conductor except for proximal and distal terminal portions. The proximal terminal portion of the conductor is connected to an electrical connector which is adapted for connection to an electronic device. The distal terminal portion of the conductor is connected to a ribbon-shaped conductive bonding member. The ribbon-shaped bonding member extends out of said aperture in the wall of the insulative tubing and extends along the outer surface of the tubing. A ribbon-shaped conductive electrode is helically wound with closely spaced turns around the outer surface of the insulative tubing and is positioned over the ribbon-shaped bonding member for substantially the entire length of the bonding member. With this configuration, a low impedance electrical connection is made between the ribbon-shaped electrode and the central conductor and between adjacent turns of the ribbon electrode. This construction also provides a defibrillation lead with an electrode of a large surface area while providing a lead with exceptional flexibility.

In another embodiment of the present invention, the endocardial lead includes a second central conductor which is connected in a similar manner, i.e., through a ribbon-shaped conductive bonding member to a second ribbon-shaped conductive electrode to thereby provide a bipolar endocardial lead.

In still another embodiment of the invention, the endocardial lead includes a third central conductor which is connected to a tip electrode in order to additionally provide the function of cardiac pacing.

BRIEF DESCRIPTION OF THE DRAWINGS

FIG. 1 is an elevational view which illustrates the endocardial lead of the present invention coupled to a cardiac pacer and defibrillator;

FIG. 2 is a cross-sectional view of the heart with the endocardial lead of the present invention positioned to provide defibrillation and pacing of the heart;

FIG. 3 is an elevational view of a portion of FIG. 1 which illustrates in more detail the construction of an electrode of the endocardial lead of the present invention; and FIG. 4 is an elevational view shown partly in cross-section of the lead of FIG. 3 taken along and in a direction of the arrows 4—4.

DETAILED DESCRIPTION OF THE DRAWINGS

Referring now to FIG. 1, the endocardial lead 10 is connected to a cardiac pacer with defibrillator 11. The cardiac pacer with defibrillator 11 may take various forms but preferably takes the form of a cardiac system which may operate in either the pacing mode or in a defibrillator mode. Accordingly, when it is desired to apply defibrillator pulses, the system is switched to that mode in order to defibrillate the heart. Once defibrillation has occurred, the system may be switched back to a pacing mode in order to assist the heart in maintaining a desired pacing rate.

More particularly, the endocardial lead 10 takes the form of a bipolar defibrillator lead having a first conductive electrode 12 being positioned toward the distal end of the lead 10 and a second conductive electrode 14 being positioned at a predetermined distance away from the first conductive electrode 12. In addition, the lead 10 includes a tip electrode 16 which is positioned at the distal end of the lead and provides the function of pacing of the heart.

The conductive electrodes 12, 14 are helically wound on an elongated flexible insulative tubing 17. The tubing 17 may take the form of a thin-walled seven French size tubing of the type which is generally utilized in angiographic catheters. The proximal end of the tubing 17 is coupled to a junction terminal 18. As illustrated, three conductive leads, 20, 22, 24 extend from the junction terminal 18 are respectively connected to the and connectors 26, 28, 30. The terminal connectors 26, 28, 30 are in turn adapted to be electrically connected to the pacer with defibrillator circuit 11. Accordingly, the temporary defibrillator lead 10 is of a construction to provide bipolar defibrillation through the conductive electrodes 12, 14, as well as a pacing function through the tip electrode 16 in conjunction with another electrode such as the electrodes 12 or 14. Each of the electrodes 12, 14, 16 are connected to the pacer with defibrillator 11 for performing the defibrillation and pacing functions.

Referring now to FIG. 2, the temporary defibrillation lead 10 is illustrated in conjunction with a human heart 32. More particularly, the conductive electrode 12 positioned near the distal end of the lead 10 is positioned against the wall of the heart. The other conductive electrode 14 which is spaced apart from the conductive electrode 12 serves to establish contact with the wall of the heart at another position so that when an electrical potential is applied to these electrodes 12, 14, an electrical current is induced in the fibrillating myocardium. The electrical current depolarizes the myocardium thereby allowing the heart to begin normal cardiac rhythm. If normal cardiac rhythm is delayed, then pacing signals are applied to the heart through the tip electrode 16 and typically through electrode 12 to thereby assist in maintaining the normal cardiac rhythm.

Referring now to FIGS. 3 and 4, the construction of the conductive electrode 12 is shown in more detail. A first aperture 34 is made in the wall of the tubing 17 at a position near one end of the conductive electrode 12 and a second aperture 36 is positioned through the wall of the tubing 17 at the other end of the conductive electrode 12.

A ribbon-shaped conductive bonding member extends from inside the tubing 17 through the aperture 36 and is positioned along the outer surface of the tubing 17. The other end of the ribbon-shaped bonding member 38 is inserted through the aperture 34 and back into the inside of tubing 17. One of the ends of a central conductor 40 is connected to the end of the ribbon-shaped bonding member and the other end of central conductor 40 is connected to one of the conductive leads 20, 22, 24.

The conductive electrode 12 is formed by tightly wrapping a ribbon-shaped conductor so as to form a helical coil about the outer surface of the tubing 17 at a position so as to overlap the bonding member 38. The tightly wound ribbon-shaped electrode 12 is in direct electrical contact with the bonding member 38 over the entire length of the bonding member 38 to thereby provide a low impedance electrical connection between the electrode 12 and the central conductor 40. In addition, with this construction technique, a very low impedance is maintained between adjacent turns of the helically wound electrode 12. The ends of the helically wound electrode 12 are inserted through a first aperture 42 and a second aperture 44 into the inside of the tubing 17 to thereby retain the electrode in a fixed position relative to the tubing 17. In addition, an adhesive may be applied over the apertures 34, 36, if desired, to further enhance the attachment of the bonding member 38 and the ribbon electrode 12 to the tubing 17.

The tip electrode is positioned at the distal end of the tubing 17 and is connected through another central conductor 46 to one of the conductive leads 20, 22, 24. As previously mentioned, the tip electrode 16 serves to apply pacing signals to the wall of the ventricle for cardiac pacing.

It should be understood that the other conductive electrode 14 is constructed similar to that of the electrode 12 and utilizes a ribbon-shaped bonding member for connection to the remaining one of the conductive leads, 20, 22, 24.

In one embodiment of the temporary defibrillator lead 10, the elongated, flexible tubing 17 was formed of a seven French size thin wall tubing. The helically wound electrodes are formed of a thin ribbon of either Elgiloy or platinum with a rectangular cross-section of 0.023 inches by 0.002 inches. When the helically wound electrodes are formed, the inside diameter of these electrodes is 0.076 inches and the outside diameter is 0.084 inches.

The electrode 12 is spaced approximately 0.400 of an inch from the distal end of the tubing 17, the electrodes 12, 16 are approximately 2.5 inches in length, and the electrode 14 is spaced approximately 2½ inches from the other electrode 12. The turns of the electrode are closely spaced with the spacing between adjacent edges of each turn being on the order of 0.001 inches. The ribbon shaped body member 38 which is covered by the ribbon-shaped conductor in an overlapping relationship, is rectangular in cross section and has a thickness of approximately 0.002 inches.

With the lead construction of the present invention, a very large surface area is obtained for each of the conductive electrodes 12, 14, however, the electrodes do not appreciably affect the overall flexibility of the plastic tubing 17. Accordingly, a defibrillator lead may be constructed which may be utilized to very effectively defibrillate a human heart due to the large surface area of the electrodes while maintaining the desired flexibility of the lead.

It should be appreciated that the electrode construction of the present invention may not only be utilized with defibrillator leads as described in the preferred embodiment, but may be used with various other types of cardiac leads such as pacing leads, leads for monitoring cardiac activity, etc.

While a specific embodiment of the present invention has been described, it should be appreciated that this embodiment was described for purposes of illustration only without any intentions of limiting the scope of the present invention. Rather the intention is that the present invention be limited not by the above description but only as is defined in the appended claims.

What is claimed is:
1. An endocardial lead comprising:
   an elongated, flexible, insulative tubing having proximal and distal ends, said insulative tubing having an aperture extending through the wall of said tubing at a predetermined position along the length of said tubing;
   an elongated, flexible, central conductor positioned within said insulative tubing, said central conductor having an insulative coating surrounding said central conductor over substantially the entire length thereof except for proximal and distal end portions of said central conductor;

the proximal end portion of said central conductor being connected to an electrical connector adapted for connection to a pulse generating device;

an elongate ribbon-shaped flat conductive bonding member extending generally parallel to the axis of said tubing on said tubing, having a length substantially greater than its width, and having one end electrically connected to said distal end portion of said central conductor within said insulative tubing, said elongate ribbon-shaped bonding member extending from said aperture and along and on the outer surface of said insulative tubing for essentially the full length of said bonding member; and a continuously wound ribbon-shaped conductive electrode having a generally rectangular cross-section and being helically wound with a plurality of closely spaced turns around the outer surface of said insulative tubing and having flat side surfaces thereof over and in direct electrical contact with said flat ribbon-shaped bonding member for substantially the entire length of said bonding member to thereby provide a low impedance electrical connection between said plurality of closely spaced turns of said ribbon shaped electrode and said central conductor and between adjacent turns of said ribbon-shaped electrode.

2. An endocardial lead as defined in claim 1 wherein said insulative tubing has at least two electrode retaining apertures which extend through the wall of said tubing, one of the ends of said ribbon-shaped electrode extending from the outer surface of said tubing through one of said retaining apertures into said tubing and the other end of said ribbon-shaped electrode extending from the outer surface of said tubing through the other one of said retaining apertures into said tubing.

3. An endocardial lead as defined in claim 2 wherein said ribbon-shaped bonding member of rectangular cross-sectional configuration has a thickness of approximately 0.002 inches.

4. An endocardial lead as defined in claim 3 wherein said ribbon-shaped conductive electrode of rectangular cross-sectional configuration has a thickness of approximately 0.002 inches.

5. An endocardial lead as defined in claim 4 wherein the spacing between edges of adjacent turns of said ribbon-shaped helically wound electrode is approximately 0.001 inches.

6. An endocardial lead as defined in claim 5 wherein said helically wound electrode is approximately 2.5 inches in length.

* * * * *